US012606551B2

United States Patent

(12) United States Patent
Guo et al.

(10) Patent No.: US 12,606,551 B2
(45) Date of Patent: Apr. 21, 2026

(54) SALT OF TETRAHYDROISOQUINOLINE DERIVATIVE, PREPARATION METHOD THEREFOR, AND MEDICAL USE THEREOF

(71) Applicants: ZHEJIANG HISUN PHARMACEUTICAL CO., LTD., Taizhou (CN); SHANGHAI ARYL PHARMTECH CO., LTD., Shanghai (CN)

(72) Inventors: Yanghui Guo, Shanghai (CN); Lichen Meng, Shanghai (CN); Xiangui Huang, Shanghai (CN); Weiwei Liao, Shanghai (CN); Yongxiang Gong, Taizhou (CN); Daiwang Xu, Shanghai (CN); Taishan Hu, Shanghai (CN); Lei Chen, Taizhou (CN)

(73) Assignees: ZHEJIANG HISUN PHARMACEUTICAL CO., LTD., Taizhou (CN); SHANGHAI ARYL PHARMTECH CO., LTD., Shanghai (CN)

( * ) Notice: Subject to any disclaimer, the term of this patent is extended or adjusted under 35 U.S.C. 154(b) by 602 days.

(21) Appl. No.: 18/012,269

(22) PCT Filed: Jun. 25, 2021

(86) PCT No.: PCT/CN2021/102261
§ 371 (c)(1),
(2) Date: Dec. 22, 2022

(87) PCT Pub. No.: WO2022/001847
PCT Pub. Date: Jan. 6, 2022

(65) Prior Publication Data

US 2023/0242522 A1 Aug. 3, 2023

(30) Foreign Application Priority Data

Jul. 1, 2020 (CN) ......................... 202010625224.7

(51) Int. Cl.
*C07D 413/14* (2006.01)

(52) U.S. Cl.
CPC .................................. *C07D 413/14* (2013.01)

(58) Field of Classification Search
CPC .................................................... C07D 413/14
USPC ......................................................... 514/307
See application file for complete search history.

(56) References Cited

U.S. PATENT DOCUMENTS

| | | | | |
|---|---|---|---|---|
| 11,384,097 | B2 * | 7/2022 | Guo | A61K 31/517 |
| 2016/0145213 | A1 | 5/2016 | Mccarthy et al. | |
| 2021/0277021 | A1 | 9/2021 | Guo et al. | |

FOREIGN PATENT DOCUMENTS

| | | | | |
|---|---|---|---|---|
| CN | 105358532 | A | 2/2016 | |
| WO | 9323378 | A1 | 11/1993 | |
| WO | 2013110135 | A1 | 8/2013 | |
| WO | 2015003223 | A1 | 1/2015 | |
| WO | 2016113668 | A1 | 7/2016 | |
| WO | WO-2019242599 | A1 * | 12/2019 | A61K 31/4725 |

OTHER PUBLICATIONS

Stahl, “The Practice of Medicinal Chemistry: 35 Preparation of water-soluble compounds through salt formation”, 2003, The Practice of Medicinal Chemistry, pp. 601-615, XP022211982 (Year: 2003).*

Serajuddin, Salt formation to improve drug solubility, Advanced Drug Delivery Reviews, 2007, vol. 59(7), pp. 603-616 (Year: 2007).*

WO 2019242599 A1 English translation, Espacenet, 2019 (Year: 2019).*

Search Report dated Jun. 10, 2024 for European patent application No. 21832154.5.

Heinrich Stahl P. ED—Wermuth C G: “The Practice of Medicinal Chemistry; 35 Preparation of water-soluble compounds through salt formation” , 2003, The Practice of Medicinal Chemistry, pp. 601-615 XP002566271.

Serajuddin et al., Advanced Drug Delivery Reviews, 59 (7), 2007, pp. 603-616, XP022211982.

International Search Report for PCT/CN2021/102261 mailed Sep. 27, 2021, ISA/CN.

* cited by examiner

*Primary Examiner* — Jeffrey H Murray
*Assistant Examiner* — Rilla Marie Samsell
(74) *Attorney, Agent, or Firm* — Xue (Robert) Xu; Apex Attorneys at Law, LLP

(57) ABSTRACT

The present invention relates to a pharmaceutically acceptable salt of (S)-2-(6-fluorobenzo[d]oxazol-2-yl)-6-methoxy-5-((5-methoxypyridin-2-yl))methoxy)-1,2,3,4-tetrahydroisoquinoline-3-carboxylic acid, a preparation method therefor, a pharmaceutical composition comprising the pharmaceutically acceptable salt thereof, and the use thereof as a therapeutic agent, in particular as an angiotensin II type-2 receptor antagonist.

4 Claims, No Drawings

SALT OF TETRAHYDROISOQUINOLINE DERIVATIVE, PREPARATION METHOD THEREFOR, AND MEDICAL USE THEREOF

CROSS REFERENCE TO RELATED APPLICATIONS

This application is the national phase of International Application No. PCT/CN2021/102261, titled "TETRAHYDROISOQUINOLINE DERIVATIVE, PREPARATION METHOD THEREFOR, AND MEDICAL USE THEREOF", filed on Jun. 25, 2021, which claims the priority to Chinese Patent Application No. 202010625224.7, titled "SALT OF TETRAHYDROISOQUINOLINE DERIVATIVE, PREPARATION METHOD THEREFOR, AND MEDICAL USE THEREOF", filed on Jul. 1, 2020 with the China National Intellectual Property Administration, which is incorporated herein by reference in entirety.

FIELD

The present invention relates to a pharmaceutically acceptable salt of (S)-2-(6-fluorobenzo[d]oxazol-2-yl)-6-methoxy-5-((5-methoxypyridin-2-yl))methoxy)-1,2,3,4-tetrahydroisoquinoline-3-carboxylic acid, a production method thereof, a pharmaceutical composition comprising the pharmaceutically acceptable salt thereof, and use thereof as a therapeutic agent, in particular as an angiotensin II type-2 receptor antagonist.

BACKGROUND

Neuropathic pain is a chronic pain disease caused by primary injury or dysfunction of the nervous system, which can be divided into peripheral neuropathic pain and central neuropathic pain according to the location of the lesion. Trauma, inflammation, infection, or compression and the like can cause neuropathic pain, such as diabetic neuropathic pain (DNP), post-herpetic neuralgia (PHN), primary neuropathy, secondary neuropathy, peripheral neuropathy, and neuropathic diseases caused by mechanical or biochemical nerve injury. At present, the drugs used in clinical treatment for neuropathic pain mainly include antiepileptic drugs, antidepressant drugs and anesthetic analgesic drugs, such as gabapentin, pregabalin, and tricyclic antidepressant drugs. However, these drugs lack of specificity, and have very limited therapeutic effect and serious side effects, including cognitive changes, sedation, nausea, and tolerance and dependence, which are far from meeting the needs for clinical drug. Therefore, it is necessary to study the pathogenesis of neuropathic pain, find clear targets for drug action, and develop new drugs that can effectively treat neuropathic pain with few adverse reactions.

Angiotensin II receptor is a G protein-coupled receptor with angiotensin II as a ligand, and it is an important part of the renin-angiotensin system. The major subtypes of the angiotensin II receptor include the type-1 receptor ($AT_1R$) and the type-2 receptor ($AT_2R$). Only about 30% of the amino acid sequences of the $AT_1R$ and $AT_2R$ are identical, but angiotensin II, as their main ligand, has a similar affinity with the two.

$AT_2R$ is abundantly expressed in various embryonic tissues and less distributed in normal tissues of adults, but its expression increases after tissue injury. $AT_2R$ is related to blood pressure regulation, nerve growth, pain control and myocardial regeneration, and drugs targeting $AT_2R$ can improve cardiovascular function and relieve neuropathic pain. The compound Olodanrigan (EMA401), developed by *Spinifex* in Australia, is a highly selective $AT_2R$ antagonist, and is currently in Phase II clinical trials. This drug candidate has a good therapeutic effect on neuropathic pain such as diabetic neuropathic pain and post-herpetic neuralgia. Meanwhile, *Spinifex* is also developing an $AT_2R$ antagonist EMA-400. WO 93/23378 discloses a method for producing Olodanrigan and EMA-400, and their structures are respectively as follows:

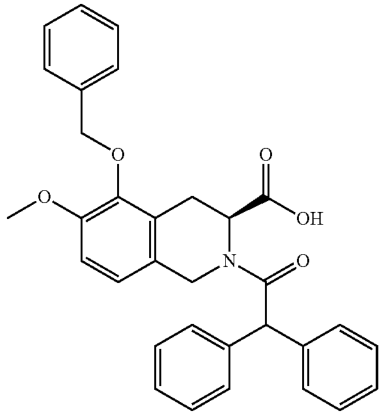

olodanrigan

EMA-400

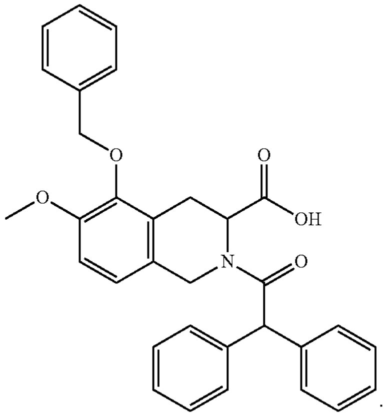

At present, a series of patent applications relating to $AT_2R$ antagonists have been disclosed, including WO2016113668, WO2015003223, WO2013110135, etc. The research and application of $AT_2R$ antagonists have made certain progress, but they are still far from meeting the needs for clinical medication, and there is still room for improvement. Therefore, it is still necessary to continue the research and development of new $AT_2R$ antagonists, especially new selective $AT_2R$ antagonists.

(S)-2-(6-fluorobenzo[d]oxazol-2-yl)-6-methoxy-5-((5-methoxypyridin-2-yl))methoxy)-1,2,3,4-tetrahydroisoquinoline-3-carboxylic acid (compound 1m) is an angiotensin II type-2 receptor antagonist, and production and biological activity thereof are disclosed in WO2019242599. However, the compound has insufficient solubility in water and unsatisfactory pharmacokinetic properties, greatly limiting its use. Therefore, how to improve its solubility and pharmacokinetic properties is still a problem in the prior art.

SUMMARY

The inventors have unexpectedly found that the salts of this compound, especially the sodium salt thereof, have particularly favorable water solubility and significantly improved pharmacokinetic properties.

Based on the above findings, the present invention provides a pharmaceutically acceptable salt of (S)-2-(6-fluorobenzo[d]oxazol-2-yl)-6-methoxy-5-((5-methoxypyridin-2-yl)) methoxy)-1,2,3,4-tetrahydroisoquinoline-3-carboxylic acid (compound 1m), a production method thereof, a pharmaceutical composition comprising the pharmaceutically acceptable salt thereof, and use thereof as a therapeutic agent, in particular as an angiotensin II type-2 receptor antagonist. Among them, the pharmaceutically acceptable salt is an alkali metal salt, a calcium salt or a magnesium salt formed by the (S)-2-(6-fluorobenzo[d]oxazol-2-yl)-6-methoxy-5-((5-methoxypyridin-2-yl))methoxy)-1,2,3,4-tetrahydroisoquinoline-3-carboxylic acid with an organic or inorganic base; the sodium salt thereof is particularly preferred.

This salt form has excellent therapeutic activity on primary neuropathy, secondary neuropathy, peripheral neuropathy, neuropathy caused by mechanical or biochemical nerve damage, post-herpetic neuralgia, diabetic neuropathic pain or related neuropathies. It has obviously improved solubility, good pharmacokinetic properties in the animal body, and low toxicity, which is suitable for producing preparations for treating neurological diseases.

(1m)

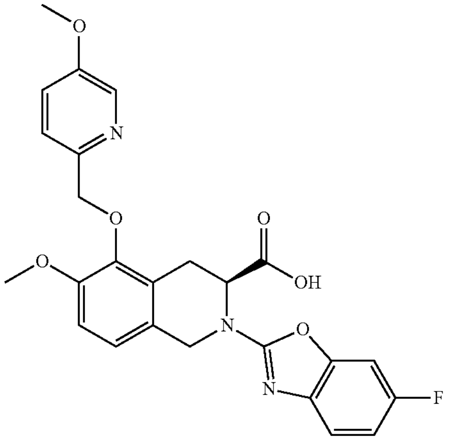

The alkali metal salt of the present invention is selected from the group consisting of a sodium salt, a potassium salt and a lithium salt; preferably a sodium salt.

Typical pharmaceutically acceptable salts of the compounds of formula (1m) in the present invention include, but are not limited to:

| Number of compound | Structure | Name |
|---|---|---|
| 1 | 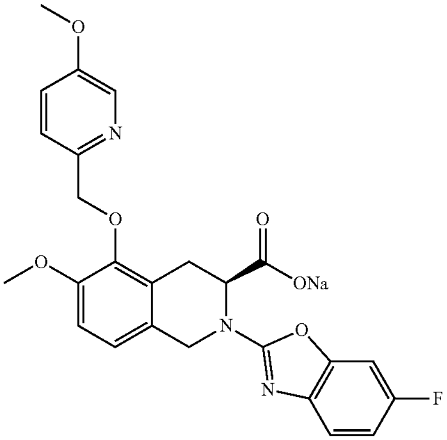 | (S)-2-(6-fluorobenzo[d]oxazol-2-yl)-6-methoxy-5-((5-methoxypyridin-2-yl)) methoxy)-1,2,3,4-tetrahydroisoquinoline-3-carboxylate sodium |
| 2 | 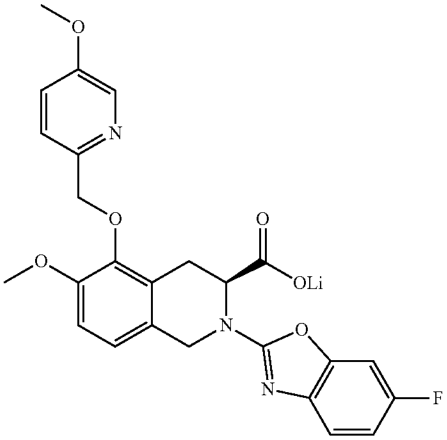 | (S)-2-(6-fluorobenzo[d]oxazol-2-yl)-6-methoxy-5-((5-methoxypyridin-2-yl)) methoxy)-1,2,3,4-tetrahydroisoquinoline-3-carboxylate lithium |

-continued

| Number of compound | Structure | Name |
|---|---|---|
| 3 | 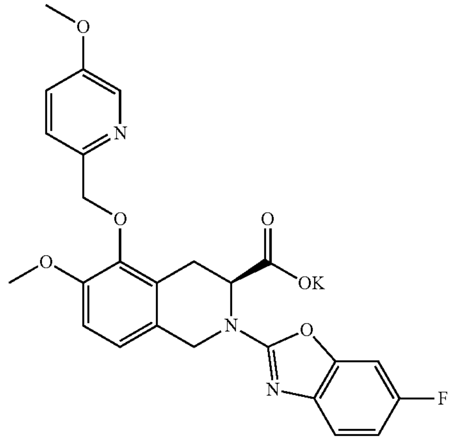 | (S)-2-(6-fluorobenzo[d]oxazol-2-yl)-6-methoxy-5-((5-methoxypyridin-2-yl))methoxy)-1,2,3,4-tetrahydroisoquinoline-3-carboxylate potassium |
| 4 | 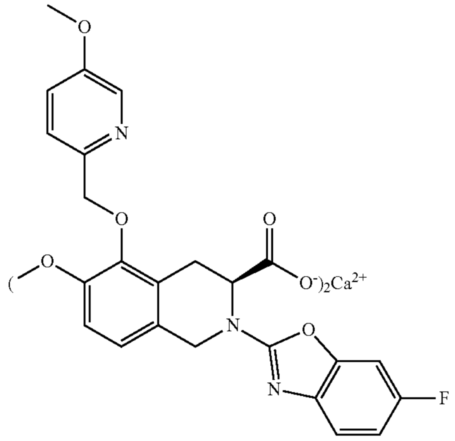 | (S)-2-(6-fluorobenzo[d]oxazol-2-yl)-6-methoxy-5-((5-methoxypyridin-2-yl))methoxy)-1,2,3,4-tetrahydroisoquinoline-3-carboxylate calcium |

The present invention also relates to a method or producing a pharmaceutically acceptable salt of the compound of formula (1m), comprising reacting the (S)-2-(6-fluorobenzo[d]oxazol-2-yl)-6-methoxy-5-((5-methoxypyridin-2-yl))methoxy)-1,2,3,4-tetrahydroisoquinoline-3-carboxylic acid with metal hydroxide, alkali metal carbonate, alkali metal bicarbonate or alkali metal alkoxide, wherein the metal hydroxide is selected from the group consisting of sodium hydroxide, potassium hydroxide, lithium hydroxide, calcium hydroxide, and magnesium hydroxide, preferably sodium hydroxide; the alkali metal carbonate is selected from the group consisting of sodium carbonate and potassium carbonate; the alkali metal bicarbonate is selected from the group consisting of sodium bicarbonate and potassium bicarbonate; the alkali metal alkoxide is selected from the group consisting of sodium methoxide, sodium ethoxide, sodium tert-butoxide, potassium methoxide, potassium ethoxide and potassium tert-butoxide, preferably sodium methoxide or sodium ethoxide.

Usually the above-mentioned production process can be carried out under conditions of cooling, normal temperature or heating. It is worth noting that the selection of reaction temperature has a certain influence on different salt-forming reactions, which is also well known to those skilled in the art. The temperature of the salt-forming reaction of the present invention is from normal temperature to the boiling point of the solvent used, and those skilled in the art can easily determine the most preferred reaction temperature for the specific salt-forming reaction through conventional technical means in the art.

The present invention also provides a pharmaceutical composition, which comprises a therapeutically effective amount of a pharmaceutically acceptable salt of the compound of formula (1m), and a pharmaceutically acceptable carrier. In addition, the present invention further provides use of the pharmaceutical composition in the production of a medicament for treating primary neuropathy, secondary neuropathy, peripheral neuropathy, neuropathy caused by mechanical or biochemical nerve damage, post-herpetic neuralgia, diabetic neuropathic pain or related neuropathies.

The present invention also provides use of a pharmaceutically acceptable salt of the compound of formula (1m) or a pharmaceutical composition thereof in the production of a medicament for treating primary neuropathy, secondary neuropathy, peripheral neuropathy, neuropathy caused by mechanical or biochemical nerve damage, post-herpetic neuralgia, diabetic neuropathic pain or related neuropathies.

The present invention also provides use of a pharmaceutically acceptable salt of the compound of formula (1m) or a pharmaceutical composition thereof in the production of an angiotensin II type-2 receptor antagonist.

The present invention also provides a method for treating primary neuropathy, secondary neuropathy, peripheral neuropathy, neuropathy caused by mechanical or biochemical nerve damage, post-herpetic neuralgia, diabetic neuropathic pain or related neuropathies, comprising administering a therapeutically effective amount of a pharmaceutically acceptable salt of the compound of formula (1m) or a pharmaceutical composition thereof to a patient in need thereof.

The present invention also provides a method for inhibiting the angiotensin II type-2 receptor, comprising contacting the angiotensin II type-2 receptor with a pharmaceutically acceptable salt of the compound of formula (1m) or a pharmaceutical composition thereof.

The present invention also provides a pharmaceutically acceptable salt of the compound of formula (1m) or a pharmaceutical composition thereof for use as a medicament for treating primary neuropathy, secondary neuropathy, peripheral neuropathy, neuropathy caused by mechanical or biochemical nerve damage, post-herpetic neuralgia, diabetic neuropathic pain or related neuropathies.

The present invention also provides a pharmaceutically acceptable salt of the compound of formula (1m) or a pharmaceutical composition thereof for use as a medicament for inhibiting angiotensin II type-2 receptor.

DETAILED DESCRIPTION OF THE INVENTION

Unless stated to the contrary, terms in the specification and claims have the following meanings.

"Pharmaceutical composition" refers to a mixture comprising a pharmaceutically acceptable salt or pro-drug of the compound described herein and other chemical components. In addition to the active pharmaceutical ingredient, it also comprises other components such as pharmaceutically acceptable carriers and/or excipients. The purpose of the pharmaceutical composition is to facilitate administration to an organism, and facilitate the absorption of the active ingredient, thereby exerting biological activity.

Method for Synthesizing the Compound of the Present Invention

In order to realize the purpose of the present invention, the present invention provides the following technical solutions:

(S)-2-(6-fluorobenzo[d]oxazol-2-yl)-6-methoxy-5-((5-methoxypyridin-2-yl))methoxy)-1,2,3,4-tetrahydroisoquinoline-3-carboxylic acid base additive salt can be produced by the following method:

reacting (S)-2-(6-fluorobenzo[d]oxazol-2-yl)-6-methoxy-5-((5-methoxypyridin-2-yl)) methoxy)-1,2,3,4-tetrahydroisoquinoline-3-carboxylic acid with metal hydroxide, alkali metal carbonate, alkali metal bicarbonate or alkali metal alkoxide in a water-miscible organic solvent;

wherein, the metal hydroxide is selected from the group consisting of sodium hydroxide, potassium hydroxide, lithium hydroxide, calcium hydroxide, and magnesium hydroxide, preferably sodium hydroxide;

the alkali metal carbonate is selected from the group consisting of sodium carbonate and potassium carbonate;

the alkali metal bicarbonate is selected from the group consisting of sodium bicarbonate and potassium bicarbonate;

the alkali metal alkoxide is selected from the group consisting of sodium methoxide, sodium ethoxide, sodium tert-butoxide, potassium methoxide, potassium ethoxide and potassium tert-butoxide, preferably sodium methoxide and sodium ethoxide.

DETAILED DESCRIPTION

The following examples are used to further describe the present invention, but these examples do not limit the scope and spirit of the present invention.

EXAMPLES

The examples provide the production and related structural identification data of the compound of formula (1m) and pharmaceutically acceptable salts thereof (for example, compound 1). It must be noted that the following examples are used to illustrate the present invention rather than limit it. 1H NMR spectra were measured with a Bruker instrument (400 MHz), and the chemical shifts were expressed in ppm. Tetramethylsilane was used as the internal standard (0.00 ppm). $^1$H NMR representation: s=singlet, d=doublet, t=triplet, m=multiplet, br=broadened, dd=doublet of doublet, dt=doublet of triplet. Coupling constants were provided in Hz.

Mass spectrum was measured by a LC/MS instrument, and the ionization mode can be ESI or APCI.

Yantai Huanghai HSGF254 or Qingdao GF254 silica gel plate was used as the silica gel plate for thin layer chromatography, the size of the silica gel plate used for thin layer chromatography (TLC) was 0.15 mm-0.2 mm, and the size of the plate used for the separation and purification of products by thin layer chromatography was 0.4 mm-0.5 mm.

200-300 mesh Yantai Huanghai silica gel was generally used as the carrier for column chromatography.

In the following examples, unless otherwise indicated, all temperatures were in degrees Celsius. Unless otherwise indicated, various starting materials and reagents were commercially available or synthesized according to known methods, and the commercially available materials and reagents were directly used without further purification. Unless otherwise specified, commercial manufacturers include but are not limited to Aldrich Chemical Company, ABCR GmbH & Co.KG, Acros Organics, Guangzan Chemical Technology Co., Ltd., Jingyan Chemical Technology Co., Ltd., etc.

$CDCl_3$: deuterated chloroform.

DMSO-$d_6$: deuterated dimethyl sulfoxide.

Unless otherwise specified in the examples, the solution in the reaction refers to an aqueous solution.

The compound was purified using thin layer chromatography or silica gel column chromatography with an eluent system, wherein the eluent system was selected from the group consisting of: A: petroleum ether and ethyl acetate system; B: dichloromethane and methanol system; C: dichloromethane and ethyl acetate system; wherein the volume ratio of the solvents varied according to the polarity of the compound, and the eluent system can also be adjusted by adding a small amount of acidic or basic reagents, such as acetic acid or triethylamine.

Example 1
(S)-2-(6-fluorobenzo[d]oxazol-2-yl)-6-methoxy-5-((5-methoxypyridin-2-yl))methoxy)-1,2,3,4-tetrahydroisoquinoline-3-carboxylate sodium
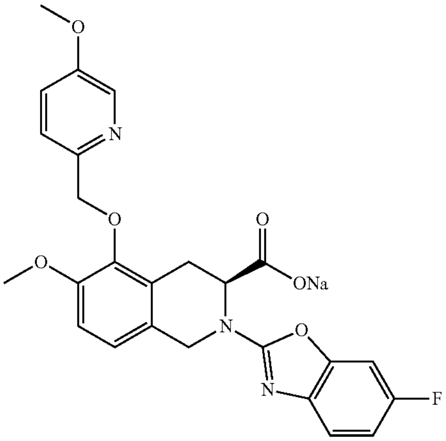
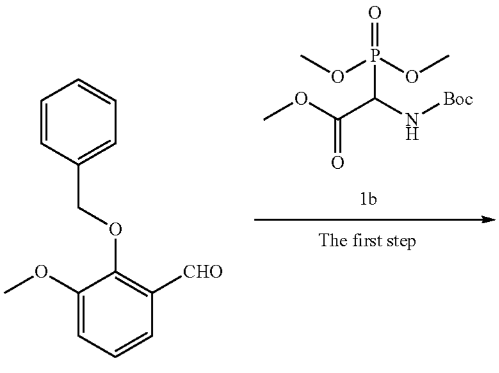
1a
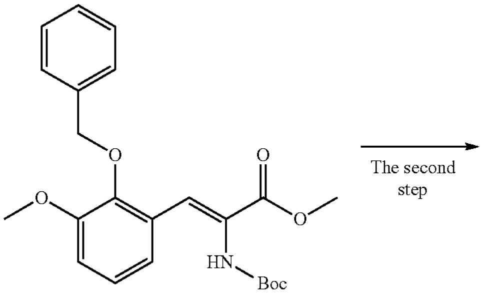
1c
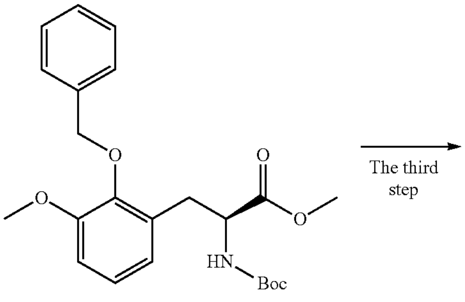
1d
-continued
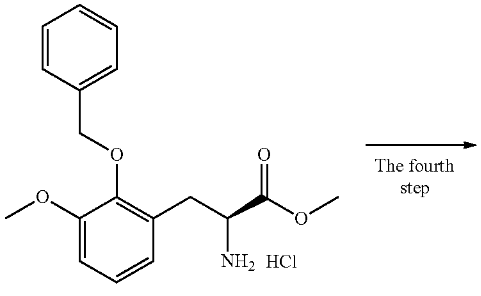
1e
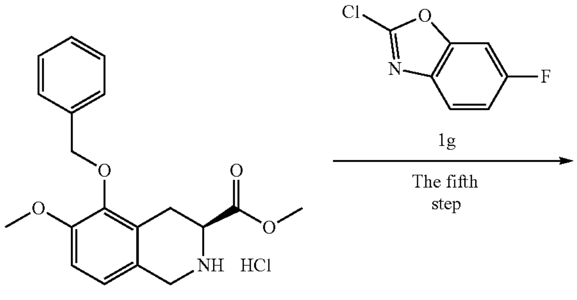
1f
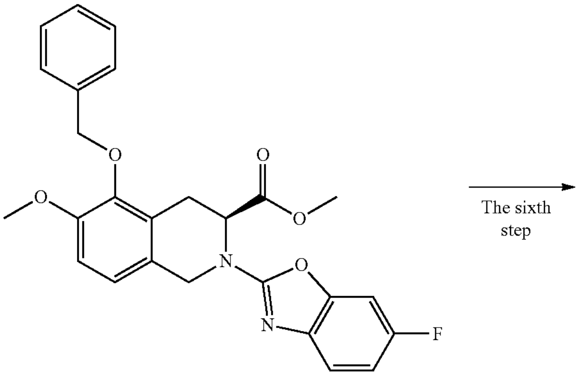
1h
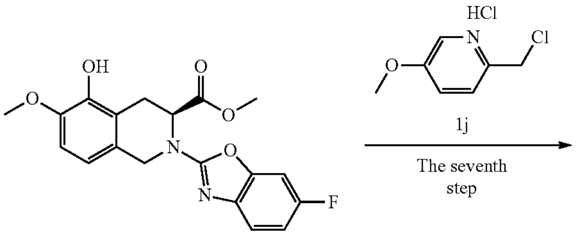
1i -continued

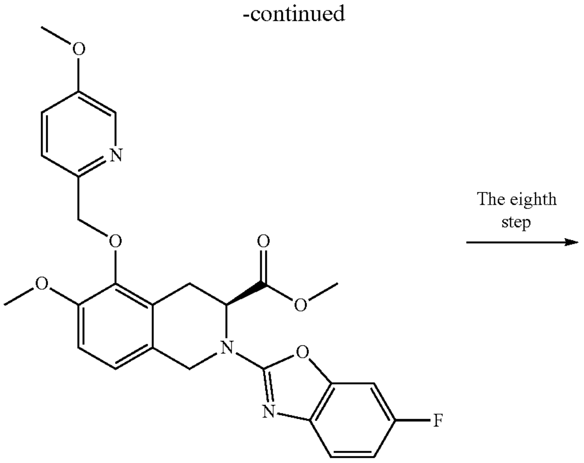

1k

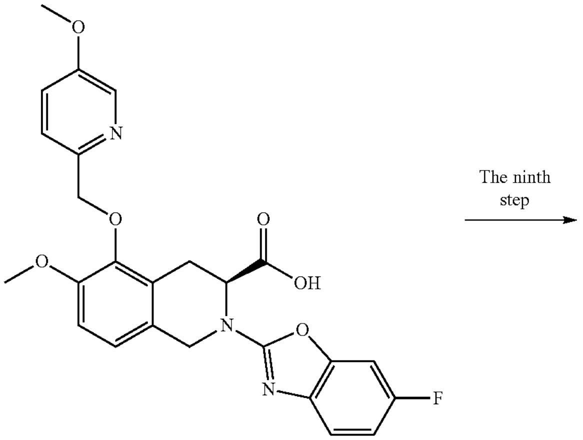

1m

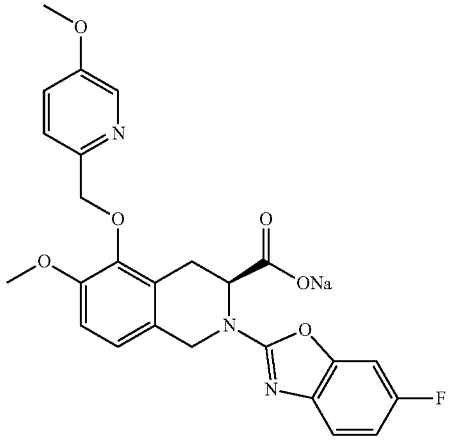

1

The First Step methyl (Z)-3-(2-(benzyloxy)-3-methoxyphenyl)-2-((tert-butoxycarbonyl)amino)acrylate (±)-BOC-A-phosphonoglycine trimethyl ester 1b (9.8 g, 33 mmol) and tetramethylguanidine (4.0 g, 34.4 mmol) were dissolved in 100 mL of tetrahydrofuran, and the reaction solution was cooled to 0° C., and added with a tetrahydrofuran solution (5 mL) of 2-(benzyloxy)-3-methoxybenzaldehyde 1a (7.0 g, 28.7 mmol) to react at room temperature overnight. After the reaction was completed, the reaction solution was concentrated under reduced pressure, ethyl acetate (40 mL) was added to dissolve the residue. The obtained mixture was washed with 10% citric acid solution (30 mL) and saturated brine (30 mL) successively, then dried over anhydrous sodium sulfate, and filtered. The obtained filtrate was concentrated under reduced pressure, and the obtained residue was purified by silica gel column chromatography (eluent: system A) to obtain methyl (Z)-3-(2-(benzyloxy)-3-methoxyphenyl)-2-((tert-butoxycarbonyl) amino) acrylate 1c (9.5 g, white solid), with a yield of 80%.

MS m/z (ESI): 314.0 [M−100]

The Second Step methyl (S)-3-(2-(benzyloxy)-3-methoxyphenyl)-2-((tert-butoxycarbonyl)amino) propionate Methyl (Z)-3-(2-(benzyloxy)-3-methoxyphenyl)-2-((tert-butoxycarbonyl)amino)acrylate 1c (5.0 g, 12.0 mmol), (R)—N-diphenylphosphine-N-methyl-(S)-2-(diphenylphosphino) ferrocenylethylamine (90 mg, 0.06 mmol) and bis(1,5-cyclooctadiene)tetrafluoroborate rhodium (I) (100 mg, 0.024 mmol) were dissolved in 50 mL of methanol. The reaction system was replaced by hydrogen gas three times, inserted with a hydrogen balloon, and reacted overnight at room temperature. After the reaction was completed, the reaction mixture was filtered, the filtrate was concentrated under reduced pressure, and the obtained residue was purified by silica gel column chromatography (eluent: system A) to obtain methyl (S)-3-(2-(benzyloxy)-3-methoxyphenyl)-2-((tert-butoxycarbonyl)amino)propionate 1d (3.2 g, colorless oil), with a yield of 64%.

MS m/z (ESI): 316.0 [M−100]

$^1$H NMR (400 MHz, DMSO-$d_6$) δ 7.48-7.32 (m, 5H), 7.23 (d, J=8.0 Hz, 1H), 6.98-6.96 (m, 2H), 6.78 (dd, J=6.4, 2.0 Hz, 1H), 4.96 (q, J=10.4 Hz, 2H), 4.20 (td, J=8.8, 5.2 Hz, 1H), 3.82 (s, 3H), 3.55 (s, 3H), 3.05 (dd, J=13.4, 5.0 Hz, 1H), 2.71 (dd, J=13.2, 10.0 Hz, 1H), 1.30 (s, 9H).

The Third Step methyl (S)-2-amino-3-(2-(benzyloxy)-3-methoxyphenyl)propionate hydrochloride Methyl (S)-3-(2-(benzyloxy)-3-methoxyphenyl)-2-((tert-butoxycarbonyl)amino) propionate 1d (3.2 g, 7.7 mmol) was dissolved in 10 mL of 1,4-dioxane, and the obtained mixture was added with a 1,4-dioxane solution of hydrogen chloride (9.6 mL, 38.5 mmol, 4M) to react at room temperature for 2 hours. After the reaction was completed, the reaction mixture was concentrated under reduced pressure to obtain methyl (S)-2-amino-3-(2-(benzyloxy)-3-methoxyphenyl) propionate hydrochloride 1e (2.7 g, white solid), with a yield of 100%.

MS m/z (ESI): 316.0 [M+1]

$^1$H NMR (400 MHz, DMSO-$d_6$) δ 8.62 (s, 3H), 7.47-7.32 (m, 5H), 7.03-7.02 (m, 2H), 6.81-6.78 (m, 1H), 4.94 (q, J=11.2 Hz, 2H), 4.04 (t, J=7.2 Hz, 1H), 3.83 (s, 3H), 3.50 (s, 2H), 3.05 (d, J=7.2 Hz, 2H).

The Fourth Step methyl (S)-5-(benzyloxy)-6-methoxy-1,2,3,4-tetrahydroisoquinoline-3-carboxylate hydrochloride Methyl (S)-2-amino-3-(2-(benzyloxy)-3-methoxyphenyl) propionate hydrochloride 1e (1.3 g, 3.7 mmol) was dissolved in 2N dilute hydrochloric acid (26 mL), then the mixture was replaced by argon gas three times, stirred at room temperature for 30 minutes, and added with an aqueous solution of formaldehyde (2.8 mL, 37 mmol, 37 wt. %) and tetrahydrofuran (5 mL) successively. The obtained mixture was replaced by argon gas again 3 times to react overnight at room temperature. After the reaction was completed, acetonitrile was added to the reaction solution, and the obtained mixed solution was concentrated under reduced pressure, which process was repeated several times, to obtain methyl (S)-5-(benzyloxy)-6-methoxy-1,2,3,4-tetrahydroisoquinoline-3-carboxylate hydrochloride 1f (400 mg, white solid), with a yield of 30%.

MS m/z (ESI): 328.0 [M+1]

$^1$H NMR (400 MHz, DMSO-$d_6$) δ 10.12 (s, 2H), 7.45-7.33 (m, 5H), 7.05 (d, J=8.8 Hz, 1H), 7.00 (d, J=8.4 Hz, 1H), 4.96 (d, J=2.0 Hz, 2H), 4.41 (dd, J=10.8, 5.2 Hz, 1H), 4.22 (q, J=15.6 Hz, 2H), 3.82 (s, 3H), 3.77 (s, 3H), 3.21 (dd, J=17.2, 5.2 Hz, 1H), 2.92 (dd, J=17.6, 11.2 Hz, 1H).

The Fifth Step methyl (S)-5-(benzyloxy)-2-(6-fluorobenzo[d]oxazol-2-yl)-6-methoxy-1,2,3,4-tetrahydroisoquinoline-3-carboxylate Methyl (S)-5-(benzyloxy)-6-methoxy-1,2,3,4-tetrahydroisoquinoline-3-carboxylate hydrochloride 1f (80 mg, 0.22 mmol), 2-chloro-6-fluorobenzo[d]oxazole 1g (37 mg, 0.22 mmol) and triethylamine (91 μL, 0.66 mmol) were dissolved in 2 mL of tetrahydrofuran to react at 50-60° C. for 5 hours. After the reaction was completed, the reaction mixture was cooled to room temperature and concentrated under reduced pressure. The obtained residue was purified by thin layer chromatography (developing solvent: system A) to obtain methyl (S)-5-(benzyloxy)-2-(6-fluorobenzo[d]oxazol-2-yl)-6-methoxy-1,2,3,4-tetrahydroisoquinoline-3-carboxylate 1h (60 mg), with a yield of 59%.

MS m/z (ESI): 462.9 [M+1]

$^1$H NMR (400 MHz, $CDCl_3$) δ 7.49-7.29 (m, 6H), 7.06 (dd, J=7.8, 2.2 Hz, 1H), 6.96-6.86 (m, 3H), 5.19 (dd, J=6.4, 2.4 Hz, 1H), 5.05 (d, J=10.8 Hz, 1H), 4.95 (d, J=11.2 Hz, 1H), 4.90 (d, J=15.6 Hz, 1H), 4.76 (d, J=15.2 Hz, 1H), 3.89 (s, 3H), 3.66-3.61 (m, 4H), 2.94 (dd, J=16.4, 6.4 Hz, 1H).

The Sixth Step methyl (S)-2-(6-fluorobenzo[d]oxazol-2-yl)-5-hydroxy-6-methoxy-1,2,3,4-tetrahydroisoquinoline-3-carboxylate Methyl (S)-5-(benzyloxy)-2-(6-fluorobenzo[d]oxazol-2-yl)-6-methoxy-1,2,3,4-tetrahydroisoquinoline-3-carboxylate 1h (600 mg, 1.3 mmol) and 10% palladium carbon (300 mg, 50% w) were dissolved in 10 mL of methanol, the reaction system was inserted with a hydrogen balloon to be replaced by hydrogen gas 4 times, and reacted at room temperature overnight. After the reaction was completed, the reaction solution was filtered through celite, and the celite was washed with a mixed solvent of ethyl acetate and methanol (V:V=1:1) (100 mL×3) and dichloromethane (100 mL×3) successively. The filtrate was concentrated under reduced pressure to obtain a crude product methyl (S)-2-(6-fluorobenzo[d]oxazol-2-yl)-5-hydroxy-6-methoxy-1,2,3,4-tetrahydroisoquinoline-3-carboxylate 1i (500 mg), with a yield of 100%.

MS m/z (ESI): 372.9 [M+1]

$^1$H NMR (400 MHz, DMSO-$d_6$) δ 8.86 (br, 1H), 7.50 (dd, J=8.8, 2.4 Hz, 1H), 7.35 (dd, J=8.6, 5.4 Hz, 1H), 7.10-7.04 (m, 1H), 6.88 (d, J=8.4 Hz, 1H), 6.74 (d, J=8.4 Hz, 1H), 5.25 (dd, J=6.4, 2.4 Hz, 1H), 4.81 (d, J=15.2 Hz, 1H), 4.63 (d, J=15.6 Hz, 1H), 3.79 (s, 3H), 3.59 (s, 3H), 3.46 (dd, J=16.2, 1.8 Hz, 1H), 3.04 (dd, J=16.8, 6.4 Hz, 1H).

The Seventh Step methyl (S)-2-(6-fluorobenzo[d]oxazol-2-yl)-6-methoxy-5-((5-methoxypyridin-2-yl) methoxy)-1,2,3,4-tetrahydroisoquinoline-3-carboxylate 2-(chloromethyl)-5-methoxypyridine hydrochloride 1j (113 mg, 0.72 mmol), potassium carbonate (149 mg, 1.08 mmol) and methyl (S)-2-(6-fluorobenzo[d]oxazol-2-yl)-5-hydroxy-6-methoxy-1,2,3,4-tetrahydroisoquinoline-3-carboxylate 1i (100 mg, 0.27 mmol) were dissolved in 6 mL of N,N-dimethylformamide successively to react at 70° C. for 6 hours. After the reaction was completed, the reaction mixture was cooled to room temperature, and added with 100 mL of ethyl acetate and 50 mL of water. The obtained mixture was subjected to layer-separation, the organic phase was collected, the aqueous phase was extracted with ethyl acetate (50 mL×2), and then the organic phases were combined. The combined organic phase was washed with saturated brine (50 mL×2), dried over anhydrous sodium sulfate, and filtered. The filtrate was concentrated under reduced pressure to obtain a crude product methyl (S)-2-(6-fluorobenzo[d]oxazol-2-yl)-6-methoxy-5-((5-methoxypyridin-2-yl)methoxy)-1,2,3,4-tetr ahydroisoquinoline-3-carboxylate 1k (133 mg), with a yield of 100%. The crude product can be further separated and purified by column chromatography (eluent: system B) for characterization.

MS m/z (ESI): 493.9 [M+1]

$^1$H NMR (400 MHz, $CDCl_3$) δ 8.30 (d, J=2.4 Hz, 1H), 7.59 (d, J=8.8 Hz, 1H), 7.32-7.29 (m, 2H), 7.07 (dd, J=7.8, 2.2 Hz, 1H), 6.96-6.86 (m, 3H), 5.21 (dd, J=6.4, 2.4 Hz, 1H), 5.12 (d, J=12.0 Hz, 1H), 5.05 (d, J=11.6 Hz, 1H), 4.91 (d, J=15.6 Hz, 1H), 4.77 (d, J=15.6 Hz, 1H), 3.89 (s, 3H), 3.87 (s, 3H), 3.67 (dd, J=16.4, 2.4 Hz, 1H), 3.63 (s, 3H), 3.02 (dd, J=16.4, 6.4 Hz, 1H).

The Eighth Step (S)-2-(6-fluorobenzo[d]oxazol-2-yl)-6-methoxy-5-((5-methoxypyridin-2-yl)methoxy)-1, 2,3,4-tetrahydroisoquinoline-3-carboxylic acid Methyl (S)-2-(6-fluorobenzo[d]oxazol-2-yl)-6-methoxy-5-((5-methoxypyridin-2-yl) methoxy)-1,2,3,4-tetrahydroisoquinoline-3-carboxylate 1k (133 mg, 0.27 mmol) was dissolved in 4 mL of tetrahydrofuran, and the mixture was added with 3 mL of a mixed solution of calcium chloride (481.74 mg, 4.34 mmol) in isopropyl alcohol and water (V:V=2:1), and then 3 mL of sodium hydroxide solution (56 mg, 1.4 mmol) to react at room temperature overnight. After the reaction was completed, the reaction mixture was added with 80 mL of ethyl acetate and 100 mL of water, and the pH of the reaction solution was adjusted to pH=5-6 with 1M dilute hydrochloric acid. The resulting mixture was subjected to layer-separation, the organic phase was collected, the aqueous phase was extracted with ethyl acetate (50 mL×2), and the organic phases were combined. The combined organic phase was washed with saturated brine (50 mL×2), dried over anhydrous sodium sulfate, and filtered. The filtrate was concentrated under reduced pressure, and the obtained residue was separated and purified with a preparative column to obtain (S)-2-(6-fluorobenzo[d]oxazol-2-yl)-6-methoxy-5-((5-methoxypyridin-2-yl)methoxy)-1,2,3,4-tetr ahydroisoquinoline-3-carboxylic acid 1m (15 mg), with a yield of 12%.

MS m/z (ESI): 479.9 [M+1]

$^1$H NMR (400 MHz, DMSO-$d_6$) δ 8.30 (d, J=2.8 Hz, 1H), 7.58 (d, J=8.4 Hz, 1H), 7.52-7.48 (m, 2H), 7.34 (dd, J=8.6, 5.0 Hz, 1H), 7.09-7.01 (m, 3H), 5.07 (dd, J=6.2, 2.6 Hz, 1H), 5.00 (d, J=11.2 Hz, 1H), 4.93 (d, J=11.2 Hz, 1H), 4.79 (d, J=15.6 Hz, 1H), 4.66 (d, J=15.2 Hz, 1H), 3.87 (s, 3H), 3.83 (s, 3H), 3.51 (dd, J=16.0, 2.4 Hz, 1H), 3.00 (dd, J=16.2, 6.6 Hz, 1H).

The Ninth Step (S)-2-(6-fluorobenzo[d]oxazol-2-yl)-6-methoxy-5-((5-methoxypyridin-2-yl)methoxy)-1, 2,3,4-tetrahydroisoquinoline-3-carboxylate sodium (S)-2-(6-fluorobenzo[d]oxazol-2-yl)-6-methoxy-5-((5-methoxypyridin-2-yl)methoxy)-1, 2,3,4-tetrahydroisoquinoline-3-carboxylic acid 1m (0.40 g, 0.84 mmol) was added to 6 mL of ethyl acetate, and the mixture was added with sodium hydroxide/ethanol solution (0.05 g/mL, 0.668 g/mL) under stirring in an ice-water bath to adjust the pH to 7~8. The solution was concentrated to dryness to obtain (S)-2-(6-fluorobenzo[d]oxazol-2-yl)-6-methoxy-5-((5-methoxypyridin-2-yl) methoxy)-1,2,3,4-tetrahydroisoquinoline-3-carboxylate sodium 1 (0.42 g), with a yield of 100%.

MS m/z (ESI): 480.2 [M+1]

$^1$H NMR (400 MHz, DMSO-$d_6$) δ 8.26 (s, 1H), 7.62 (d, J=8.5 Hz, 1H), 7.46 (d, J=8.6 Hz, 1H), 7.38 (d, J=8.4 Hz, 1H), 7.24 (dd, J=8.2, 4.9 Hz, 1H), 7.01-6.90 (m, 3H), 4.93 (s, 2H), 4.71 (s, 2H), 4.66 (d, J=5.5 Hz, 1H), 3.84 (s, 3H), 3.79 (s, 3H), 3.67 (d, J=16.1 Hz, 1H), 2.78 (dd, J=16.1, 6.4 Hz, 1H).

Example 2

(S)-2-(6-fluorobenzo[d]oxazol-2-yl)-6-methoxy-5-((5-methoxypyridin-2-yl)methoxy)-1, 2,3,4-tetrahydroisoquinoline-3-carboxylate lithium

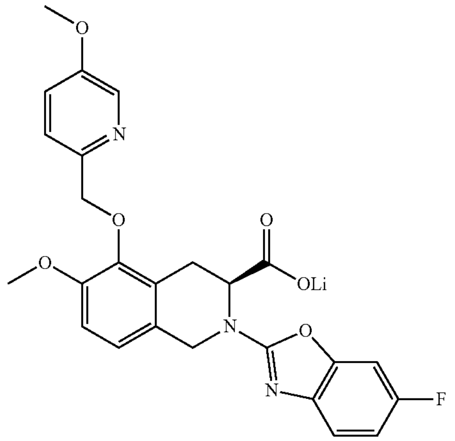

(S)-2-(6-fluorobenzo[d]oxazol-2-yl)-6-methoxy-5-((5-methoxypyridin-2-yl)methoxy)-1, 2,3,4-tetrahydroisoquinoline-3-carboxylic acid 1m (0.20 g, 0.42 mmol) was added to 6 mL of ethyl acetate, and the mixture was added with lithium hydroxide/ethanol solution (0.2 M, 2.1 mL) under stirring in an ice-water bath to adjust the pH to 7~8. The solution was concentrated to dryness to obtain (S)-2-(6-fluorobenzo[d]oxazol-2-yl)-6-methoxy-5-((5-methoxypyridin-2-yl)methoxy)-1,2,3,4-tetrahydroisoquinoline-3-carboxylate lithium 2 (0.205 g), with a yield of 100%.

MS m/z (ESI): 480.2 [M+1]

Example 3

(S)-2-(6-fluorobenzo[d]oxazol-2-yl)-6-methoxy-5-((5-methoxypyridin-2-yl)methoxy)-1,2,3,4-tetrahydroisoquinoline-3-carboxylate potassium

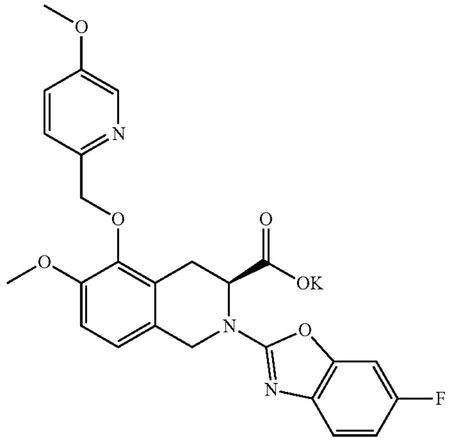

(S)-2-(6-fluorobenzo[d]oxazol-2-yl)-6-methoxy-5-((5-methoxypyridin-2-yl)methoxy)-1, 2,3,4-tetrahydroisoquinoline-3-carboxylic acid 1m (0.20 g, 0.42 mmol) was added to 6 mL of ethyl acetate, and the mixture was added with potassium hydroxide/ethanol solution (0.2 M, 2.1 mL) under stirring in an ice-water bath to adjust the pH to 7~8. The solution was concentrated to dryness to obtain (S)-2-(6-fluorobenzo[d]oxazol-2-yl)-6-methoxy-5-((5-methoxypyridin-2-yl)methoxy)-1,2,3,4-tetrahydroisoquinoline-3-carboxylate potassium 3 (0.215 g), with a yield of 100%.

MS m/z (ESI): 480.2 [M+1]

Example 4

(S)-2-(6-fluorobenzo[d]oxazol-2-yl)-6-methoxy-5-((5-methoxypyridin-2-yl)methoxy)-1,2,3,4-tetrahydroisoquinoline-3-carboxylate calcium

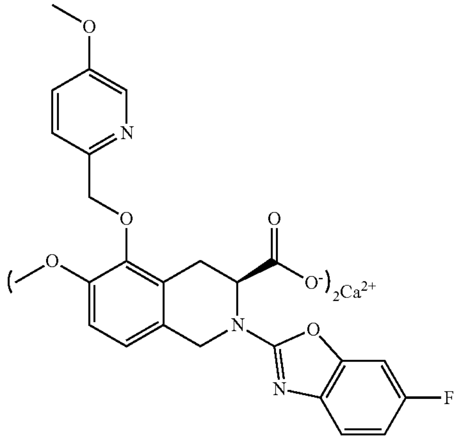

(S)-2-(6-fluorobenzo[d]oxazol-2-yl)-6-methoxy-5-((5-methoxypyridin-2-yl)methoxy)-1, 2,3,4-tetrahydroisoquinoline-3-carboxylic acid 1m (0.20 g, 0.42 mmol) was added to 20 mL of tetrahydrofuran, and the mixture was added with calcium hydroxide/water solution (0.01 M, 21 mL) under stirring in an ice-water bath to adjust the pH to 7~8. The solution was concentrated to dryness to obtain (S)-2-(6-fluorobenzo[d]oxazol-2-yl)-6-methoxy-5-((5-methoxypyridin-2-yl) methoxy)-1,2,3,4-tetrahydroisoquinoline-3-carboxylate calcium 4 (0.208 g), with a yield of 100%.

MS m/z (ESI): 480.2 [M+1]

Test Example

Solubility Test

According to the conventional method for solubility assay, the solubility of the compounds of the present invention in the following four different systems was tested: phosphate salt buffer PBS (pH7.4), methanol, 0.1% HCl and water. The results are shown in the following table:

| Number of compound | Solubility value (mg/mL) | | | |
|---|---|---|---|---|
| | PBS (pH 7.4) | Methanol | 0.1% HCl | Water |
| Compound 1m | 0.15 | 0.34 | 0 | 0.03 |
| Compound 1 | 8.69 | >10 | 0 | 6.41 |

Conclusion: The solubility of the sodium salt of the compound of the present invention (compound 1) was significantly improved compared to the free acid thereof (compound 1m).

It can be seen from the results in the above table that compared with compound 1m, the solubility of sodium salt compound 1 in water was increased by more than 200 times, which result is unexpected.

Biological Evaluation

Test Example 1 Test of the antagonistic activity of the compounds of the present invention against human $AT_2R$ ligand binding.

Angiotensin II Type-2 receptor (ATR) is involved in neuronal differentiation and regeneration, cell proliferation and angiogenesis, and maintenance of bone mass. ATR inhibitors can be used for treating pain and abnormal neuroregenerative diseases, inhibiting the proliferation of tumor cells and increasing bone mass. In the following methods, the degree of antagonism of the compounds of the present invention against $AT_2R$ was studied through $AT_2$ ligand binding assay.

1. Reagents and Consumables

| Materials and reagents | Manufacturer | Catalog number |
|---|---|---|
| Tag-lite Angiotensin AT2 labeled Cells, ready-to-use (transformed & labeled), 200 tests* (384-well small volume white plate, 20 ul) | Cisbio | C1TT1AT2 |
| Angiotensin AT2 Receptor red agonist Fluorescent Ligand, 5000 test (384-well small volume plate, 20 ul) | Cisbio | L0007RED |
| Tag-lite Buffer (5X concentrate), 100 mL | Cisbio | LABMED |
| Angiotensin II human (CAS: 4474-91-3) DRVYIHPF, 10 mg, MW: 1046.18 | MedChem Express | HY-13948 |
| **Consumables** | **Manufacturer** | **Article number** |
| 384-well low volume plate (40 plates/box) | Greiner | 784075 |
| Echo qualified 384-well polypropylene microplate, clear, flat bottom (100 plates/case) | LABCYTE | P-05525 |
| 384-well round bottom, no lid, non-sterile, polypropylene (100 plates/case) | Corning | 3657 |
| 96-well conical btm PP Plt nature RNASE/Dnase-free plate (120 plates/case) | ThermoFisher | 249944 |

2. Reagent Preparation (1) 10 mM angiotensin II human: 10 mg angiotensin II human (purity 99.09%) was dissolved in 0.947 mL of deionized water, and the obtained solution was aliquoted and stored at −80° C.;

(2) Preparation of stock solution of the compound:

According to standard methods, test compounds (compound 1m and compounds 1-4) were respectively dissolved in dimethyl sulfoxide to be prepared into stock solutions of 10 mM.

(3) Tag-lite angiotensin receptor red agonist: Tag-lite angiotensin receptor red agonist was prepared into a stock solution of 8600 nM, which was then aliquoted and stored at −80° C.;

(4) 1×Tag-Lite Buffer (TLB): 5×TLB was diluted to 1×TLB with deionized water.

3. Experimental Steps (1) An appropriate amount of 1×TLB was prepared and mixed well for later use;

(2) The test compound was subjected to 5-fold dilution with a total of 10 concentration gradients;

(3) The diluted compound in step (2) was transferred to a working plate (3657, Corning) at 160 nL/well, 200 g at room temperature for 1 minute;

(4) 40 μl of 1×TLB was added to the above working plate, then the plate was centrifuged at 200 g for 1 minute at room temperature, the solution in the plate was shaken with a shaker for 15 minutes to be mixed evenly, and then the plate was centrifuged at 200 g for 1 minute at room temperature for later use (the working concentration of the compound was 4×);

(5) Tag-lite angiotensin receptor red agonist (8600 nM stock solution) was diluted to 12 nM with 1×TLB for later use;

(6) 5 mL of 1×TLB was added into a 15 mL centrifuge tube;

(7) 1 tube of frozen Tb-labeled-$AT_2R$ cells was thawed in a 37° C. water bath until the ice was completely thawed (1-2 minutes);

(8) The thawed cells were quickly transferred to 1×TLB in step (6), and the mixture was mixed gently, and then centrifuged at 1200 g for 5 minutes at room temperature;

(9) The supernatant was gently discarded, the cells were resuspended with 1 mL of 1×TLB, the suspension was mixed evenly, and then added with 1.7 mL of 1×TLB, and the mixture was mixed evenly and kept at room temperature for later use;

(10) 10 μL of cells were added to each test well, and the plate was centrifuged at 200 g for 3 seconds at room temperature. 5 μL of the 4× working solution of the compound in step (4) was added to the corresponding well. 5 μL of diluted 4×Tag-lite angiotensin receptor red agonist in step (5) was added to each test well.

(11) The reaction plate was centrifuged at 200 g for 1 minute at room temperature, then kept still at room temperature 25° C. for 1 hour, and centrifuged at 200 g for 1 minute at room temperature. Data were collected using Envision HTRF microplate reader, and $IC_{50}$ was calculated using nonlinear fitting formula.

(12) Similarly, the $IC_{50}$ of the antagonistic activity of the compounds of the present invention against $AT_1R$ was tested according to basically the same method, except that Tb-labeled-$AT_2R$ cells were replaced by Tb-labeled-$AT_1R$ cells.

4. Experimental Results

The $IC_{50}$ values of the antagonistic activity of the compounds of the present invention against $AT_2R$ are shown in the table below.

| Number of compound | $IC_{50}$ (nM)/$AT_2R$ | $IC_{50}$ (μM)/$AT_1R$ |
|---|---|---|
| Compound 1m | 10 | >10 |
| Compound 1 | 6 | >10 |

Conclusion: (1) The sodium salt of the compound of the present invention (compound 1) had a significant antagonistic activity on $AT_2R$ compared to the free acid thereof (compound 1m);

(2) For antagonism against $AT_1R$, the sodium salt of the compound of the present invention (compound 1) and the free acid thereof (compound 1m) had $IC_{50}$ values >10 μM, showing no antagonistic activity against $AT_1R$;

Therefore, the compounds of the present invention have highly selective antagonism against $AT_2R$.

Pharmacokinetic Assay

1. The Purpose of the Experiment

SD rats were taken as the test animals, and the compounds of the present invention were administrated to the rats by intravenous injection or gavage. Then the drug concentrations in the plasma at different times were measured using LC/MS/MS method to study the pharmacokinetic characteristics of the compounds of the present invention in rats.

2. Experimental Method 2.1. Experimental Drugs and Animals

Compound 1m and Compounds 1-4.

Six healthy adult Sprague Dawley (SD) male rats were purchased from Vital River Laboratory Animal Technology Co., Ltd.

2.2 Drug Preparation and Administration (1) Drug Preparation:

76.32 mg of compound 1m was weighed and dissolved in 12.72 mL of 0.5% sodium carboxymethyl cellulose (CMC-Na), the mixture was mixed by vortex for 1 minute until the compound was completely suspended, and the final prepared concentration was 6 mg/mL;

76.61 mg of compound 1 was weighed and dissolved in 12.768 mL of 0.5% sodium carboxymethyl cellulose (CMC-Na), the mixture was mixed by vortex for 1 minute until the compound was completely suspended, and the final prepared concentration was 6 mg/mL.

Compounds 2 to 4 were weighed and dissolved in an appropriate amount of 0.5% sodium carboxymethyl cellulose (CMC-Na), the mixture was mixed by vortex for 1 minute until the compound was completely suspended, and the final prepared concentration was 6 mg/mL.

(2) Administration

Six healthy adult SD rats, half male and half female, were divided into 2 groups, 3 rats in each group. The rats were fasted overnight, and then intragastrically administered (po) with the compound 1m or compounds 1 to 4 of the present invention at a dose of 60 mg/kg.

2.3 Sample Collection

About 0.25 mL of blood was collected from the jugular vein before the administration and 0.25 hours, 0.5 hours, 1 hour, 2 hours, 4 hours, 6 hours, 8 hours and 24 hours after the administration, and heparin sodium was used for anticoagulation. The blood samples were placed on ice after collection, and then centrifuged to separate the plasma (centrifugation conditions: 7000 rpm, 5 minutes). The collected plasma was stored below −70° C. until analysis.

2.4 Sample Pretreatment

300 μL of methanol (comprising internal standard working solution, Loratadine 800 ng/mL) was added to 100 μL of plasma sample, then the mixture was mixed by vortex for 5 minutes, then the obtained mixture was centrifuged at 10,000 rpm for 10 minutes, and 1 μL of the resulting mixture was taken and subjected to LC-MS/MS analysis.

3. Pharmacokinetic Parameter Results

The pharmacokinetic parameters of the salt of the compound of the present invention and the positive control compound (compound 1m) are shown in the table below.

| | Pharmacokinetic experiments | | | | |
|---|---|---|---|---|---|
| Number of compound | Administration method Administration dosage | Blood concentration Cmax (μg/mL) | Area under the curve $AUC_{0-\infty}$ (μg · h/mL) | Half life T½(h) | Residence time MRT(h) |
| Compound1m | PO (60 mg/kg) | 2.4 ± 0.53 | 22.2 ± 9.1 | 3.73 ± 1.25 | 6.13 ± 1.13 |
| Compound1 | PO (60 mg/kg) | 127.1 ± 12.7 | 328.2 ± 53.2 | 3.57 ± 0.85 | 2.59 ± 0.41 |

Conclusion: The sodium salt of the compound of the present invention (compound 1) had significantly improved plasma concentration and area under the curve compared with the free acid thereof (compound 1m), wherein the plasma concentration was increased by more than 50 times, and the area under the curve was increased by 14 times. Surprisingly, compared with other salts (such as lithium salt, potassium salt, calcium salt, and magnesium salt) of the present invention, the sodium salt of the present invention had significant pharmacokinetic properties, and significantly improved plasma concentration and area under the curve, showing unexpected technical effects.

The invention claimed is:

1. A sodium salt, which has the following structure:

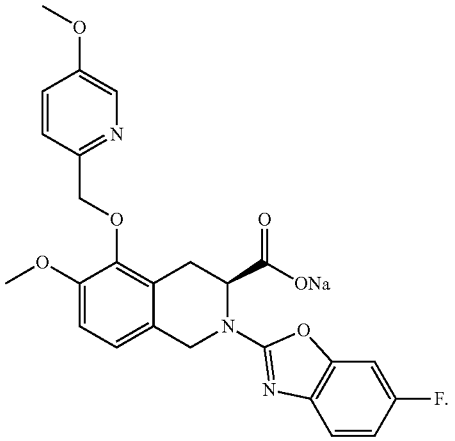

2. A pharmaceutical composition comprising a therapeutically effective amount of sodium salt according to claim 1 and a pharmaceutically acceptable carrier.

3. A method for treating or preventing primary neuropathy, secondary neuropathy, peripheral neuropathy, neuropathy caused by mechanical or biochemical nerve damage, post-herpetic neuralgia, diabetic neuropathic pain or related neuropathies, comprising administering the sodium salt according to claim 1 to a subject in need thereof.

4. A method for inhibiting an angiotensin II type-2 receptor, comprising administering the sodium salt according to claim 1 to a subject in need thereof.

* * * * *